United States Patent [19]
Schön et al.

[11] Patent Number: 5,334,742
[45] Date of Patent: Aug. 2, 1994

[54] PROCESS FOR THE CONTINUOUS PREPARATION OF DIARYL CARBONATES FROM DIALKYL CARBONATES

[75] Inventors: Norbert Schön; Reinhard Langer; Hans-Josef Buysch, all of Krefeld; Paul Wagner, Düsseldorf, all of Fed. Rep. of Germany

[73] Assignee: Bayer Aktiengesellschaft, Leverkusen, Fed. Rep. of Germany

[21] Appl. No.: 103,931

[22] Filed: Aug. 6, 1993

[30] Foreign Application Priority Data

Aug. 13, 1992 [DE] Fed. Rep. of Germany ....... 4226755

[51] Int. Cl.$^5$ .............................................. C07C 69/96
[52] U.S. Cl. ................................................... 558/274
[58] Field of Search ......................................... 558/274

[56] References Cited

U.S. PATENT DOCUMENTS 4,410,464 10/1983 Hallgren .............................. 558/274

FOREIGN PATENT DOCUMENTS 0461274 12/1991 European Pat. Off. .
3308921 9/1983 Fed. Rep. of Germany .

Primary Examiner—Mary C. Lee
Assistant Examiner—Michael G. Ambrose
Attorney, Agent, or Firm—Sprung Horn Kramer & Woods

[57] ABSTRACT

Diaryl carbonates are prepared by reaction from dialkyl carbonates and phenols using conventional transesterification catalysts in a specific mass-coupled and energy-coupled combination of columns, for example according to FIG. 1, in which the reference numerals have the meaning specified in the description.

20 Claims, 4 Drawing Sheets

PROCESS FOR THE CONTINUOUS PREPARATION OF DIARYL CARBONATES FROM DIALKYL CARBONATES

BACKGROUND OF THE INVENTION

1. Field of the Invention

The invention relates to a continuous process for the preparation of diaryl carbonates from dialkyl carbonates and phenols, using conventional transesterification catalysts, which is characterised in that the starting materials are reacted in a specific, mass-coupled and energy-coupled combination of columns.

2. Description of the Related Art

The preparation of aromatic and aliphatic-aromatic esters of carbonic acid (carbonates) by transesterification, starting from aliphatic esters of carbonic acid and phenols, is known in principle. This is an equilibrium reaction, the position of the equilibrium being almost completely displaced in the direction of the aliphatically substituted carbonates. Therefore, it is relatively easy to prepare aliphatic carbonates from aromatic carbonates and alcohols. However, in order to carry out the reaction in reverse in the direction of aromatic carbonates, it is necessary effectively to displace the highly unfavourably situated equilibrium, where not only do highly active catalysts have to be used, but also an expedient procedure has to be used.

For the transesterification of aliphatic carbonic acid esters with phenols, a multiplicity of effective catalysts have been recommended, such as for example alkali metal hydroxides, Lewis acid catalysts selected from the group comprising the metal halides (DE-OS (German Published Specification) 25 28 412 and DE-OS (German Published Specification) 25 52 907), organotin compounds (EP 879, EP 880, DE-OS (German Published Specification) 34 45 552, EP 338 760), lead compounds (JP-57/176 932), Lewis acid/protonic acid catalysts (DE-OS (German Published Specification) 34 45 553). In the known processes, the transesterification is carried out in a batchwise-operated reactor at atmospheric pressure or at superatmospheric pressure, with or without an additional separation column. In this case, even with the most active catalysts, reactions times of many hours are required until even only moderate conversions of approximately 50% of phenol are achieved. Thus in the batchwise-operated transesterification of phenol with diethyl carbonate at 180° C. using various organotin compounds, as are described in DE-OS (German Published Specification) 34 45 552, yields of diphenyl carbonate in an order of magnitude above 20% are only achieved after a reaction time of approximately 24 hours; in the batchwise-operated transesterification of phenol and dimethyl carbonate with the aid of organotin catalysts as are described in EP-879, the phenol conversion is 34% of the theoretical value after 30 hours.

This means that, because of the unfavourable thermodynamic conditions, the described transesterification reactions in tanks or pressurised autoclaves, even when highly active catalyst systems are used, can only be carried out highly disadvantageously in the sense of an industrial process, since very poor space-time yields and high residence times at high reaction temperatures are obtained, where because of the incomplete transesterification a high distillation effort must additionally be applied which requires further energy.

Such procedures are also particularly disadvantageous since, even using highly selective transesterification catalysts, at the high temperatures and long residence times of many hours, a noticeable-proportion of side-reactions occurs, for example ether formation and elimination of carbon dioxide.

It has therefore been attempted to displace the reaction equilibrium as rapidly as possible in the direction of the desired products by adsorption of the alcohol produced during the transesterification on molecular sieves (DE-OS (German Published Specification) 33 08 921). From the description of this reaction it is evident that a large amount of molecular sieve is required for the adsorption of the reaction alcohol, which greatly exceeds the amount of alcohol being liberated. In addition, the molecular sieves used must be regenerated after just a short time and the rate of conversion to the alkyl aryl carbonate intermediates is relatively low. Even this process, therefore, does not seem to be advantageously usable industrially.

It is known to carry out equilibrium reactions, in particular esterifications and transesterifications, in columns and to displace them in this manner advantageously in the direction of product formation (e.g. U. Block, Chem.-Ing.-Techn. 49, 151 (1977); DE-OS (German Published Specification) 3 809 417; B. Schleper, B. Gutsche, J. Wnuck and L. Jeromin, Chem.-Ing.-Techn. 62, 226 (1990); Ullmanns Encyclopädie der techn. Chemie [Encyclopedia of Industrial Chemistry], 4th edition, volume 3, pp. 375 ff. 1973; ibid. 5th edition, volume B4, pp. 321,1992).

In EP 0 461 274 (WO 91/09832), a continuous transesterification process is described for the preparation of aromatic carbonates in one or more multi-stage columns connected one after the other, dialkyl carbonates or alkyl aryl carbonates, being reacted with phenols and the readily volatile products, that is reaction alcohols and dialkyl carbonates, being withdrawn at the head of the columns and the high-boiling products, that is aryl carbonates, being withdrawn at the foot of the columns.

An already known process principle, carrying out transesterification reactions in columns, is thus being applied here to a specific problem, that is to the transesterification of alkyl carbonates to give aryl carbonates. However, particular engineering measures which permit the transesterification to be carried out more advantageously, matching the apparatuses and procedures to the abovementioned special problems of this difficult transesterification, are not given. Thus, for example, the manner of metering the two starting materials-alkyl carbonate and aromatic hydroxyl compound-is not clearly defined and neither is any advantageous technique emphasised. In a technique according to Diagram 1 of EP 0 461 274, for example, mixtures of these two starting materials are fed into the upper part of the column, the low-boiling reaction products, that is alcohols and unreacted dialkyl carbonate, are withdrawn at the head of the column and the high-boiling reaction products alkyl aryl carbonates and diaryl carbonates are withdrawn, together with unreacted dialkyl carbonates and aromatic hydroxyl compounds, at the foot of the column. In the technique according to Diagram 2 of EP 0 461 274, mixtures of alkyl carbonates and aromatic hydroxyl compounds are supplied at two different points of the column, that is at the upper and lower third of the column, and starting material/product mixtures are withdrawn as in the technique according to Diagram 1 of EP 0 461 274. Neither in the disclosure nor in the examples is a clear differentiation made between conducting the starting materials in co-current and counter-current, although they can have a great influence on the result of the process.

Furthermore, the influence of temperature, pressure, catalyst concentration and liquid residence time is not considered, but only very broad ranges are quoted, even in the restricted claims; for example, temperature ranges from 100° to 280° C., pressure ranges from 0.1 to 200 bar, catalyst concentrations from 0,001 to 50% by weight and liquid residence times from 0.05 to 2 h are quoted.

Different procedures to be preferred in each case for the individual reactions occurring in the conversion of dialkyl carbonates to diaryl carbonates, for example the first transesterification stage from dialkyl carbonates with aromatic hydroxyl compounds to give alkyl aryl carbonates according to Equation 1, the second transesterification stage to give diaryl carbonates according to Equation 2 and the disproportionation according to Equation 3, are not considered in the disclosure.

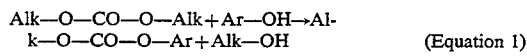  (Equation 1)

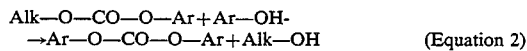  (Equation 2)

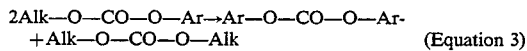  (Equation 3)

(Alk=alkyl, Ar=aryl)

The embodiments of this EP 461 274 lead those skilled in the art to the conclusion that, although the transesterification of phenols with dialkyl carbonates can be carried out continuously in a known manner by known processes in columns, it is immaterial by which variant, whether at high or low temperature, in co- or counter-current, at low or high pressure, at large or small molar ratios etc. In brief, one must conclude therefrom that, in the case of this particular transesterification problem, there are no possibilities for improvement and for a more advantageous procedure.

Thus just the examples quoted can be used to evaluate the actual value of this EP.

From these examples it can be seen that in the transesterification of dialkyl carbonates with phenols, even at relatively high temperatures, at elevated pressure and even at molar excesses of dialkyl carbonate of more than 3, only low conversions in the range from 10 to 15% (in the best case approximately 19%) and, especially, only very low space-time yields up to 0.02 kg $1^{-1}h^{-1}$ are achieved. This is surprising, especially since very large colons have been used, among them even a 20-plate column 6 m in length and approximately 300 l in volume. The higher phenol conversion achievable by dialkyl carbonate excesses must in any case be gained, for stoichiometric reasons, at the expense of lower dialkyl carbonate conversions. This means that the dialkyl carbonate withdrawn at the head contains only very low amounts of alcohol and thus, in an industrial process, considerably more unreacted starting product must be circulated and separated off from the small amounts of reaction alcohol. The low space-time yields, for a given production amount per unit time, would make very large reactors and very large distillation capacities necessary.

Although the disproportionation reaction of alkyl aryl carbonates performed in a downstream second column in accordance with Equation 3 does proceed with higher yields, such a disproportionation of alkyl aryl carbonates, in comparison with the further transesterification with phenols, should be seen as less advantageous for an industrial synthesis of diaryl carbonates, since only every second alkyl aryl carbonate molecule is converted into the diaryl carbonate end product and the other half is returned to the starting dialkyl carbonate.

For instance, Examples 22 to 30 of EP 0 461 274, in which reactions are described in two columns connected one after the other and the composition of the head product from the second column is mentioned as feed stream No. 6 in Diagram 4 or 5, it is clear that, in spite of the presence of considerable amounts of phenols, no alcohol is formed in the second reaction stage and accordingly the proportion of the second transesterification stage according to Equation 2 is equal to zero.

In an industrial process for the preparation of diaryl carbonates, specifically of diphenyl carbonate from dimethyl carbonate and phenol, it is not only the phenol conversion which is of importance but also the dimethyl carbonate amount which is necessary to achieve a certain phenol conversion, and the dimethyl carbonate conversion resulting from this. In practice, only low dimethyl carbonate conversions and thus low methanol concentrations in the dimethyl carbonate at the column head will be able to be achieved by such a process variant, for example those of 5 to 10% by weight of methanol. However, in EP 461 274, pure dimethyl carbonate or diethyl carbonate is used without restrictions as starting material. From the viewpoint of the low conversions obtained of dialkyl carbonates of only a few percent, this is understandable and certainly absolutely necessary since, because of the unfavourable equilibrium position, if alcohol-containing dialkyl carbonates were used the conversion rates would be still lower and thus industrially unacceptable. However, methanol forms with dimethyl carbonate an azeotrope of the composition 70% by weight of methanol and 30% by weight of dimethyl carbonate, which can be separated only with great distillation effort.

However, the removal of very small amounts of the reaction methanol from the dimethyl carbonate product stream requires a particularly high separation effort, as a result of which the return of the unreacted dimethyl carbonate into the transesterification process in pure form can only be achieved with very great effort. This is also of particular economic importance, since, because of the only small dimethyl carbonate conversion rates which can be achieved during a reactor pass, the circulated amounts of dimethyl carbonate are very large.

The aim of an improved transesterification process for the preparation of diaryl carbonates from dialkyl carbonates and phenols would therefore have to be, firstly, to make significant amounts of alcohols tolerable in the dialkyl carbonate starting material stream and, secondly, to promote the transesterification stage according to Equation 2, that is the transesterification of phenol with alkyl aryl carbonate to give diaryl carbonate and to repress the disproportionation of alkyl aryl carbonate.

It can be deduced from the mass action law that even small amounts of alcohols would react with the aryl carbonates already formed, because of the highly unfavourably situated transesterification equilibrium, again in the direction of the starting materials. There therefore seem to be no prospect of realising the above-mentioned first aim. The authors of EP 0 461 274 have apparently also assumed this.

The transesterification of an alkyl aryl carbonate with phenol to give diaryl carbonate according to Equation 2 is, according to the results of EP 461 274, apparently disadvantaged in comparison with the disproportionation of two alkyl aryl carbonate molecules according to Equation 3, or even completely suppressed. It thus appears to be highly questionable whether the second aim can be achieved. For an industrial synthesis, moreover, an increase of the space-time yields above those mentioned in EP 461 274 should be attempted as a third aim in order to decrease the size of the apparatuses. For this as well, EP 461 274 offers no solution.

SUMMARY OF THE INVENTION

Surprisingly, it has now been found that the transesterification of phenols with dialkyl carbonates can be carried out in a multistage process in which the desired aims can be realised and, moreover, an optimal energy utilisation is achieved. For this purpose, a mass-coupled and energy-coupled combination of two column-type reactors is used.

The invention therefore relates to a process for the preparation of diaryl carbonates of the formula I $$Ar^1\text{—}O\text{—}CO\text{—}O\text{—}Ar^1 \qquad (I)$$

in which $Ar^1$ denotes unsubstituted phenyl, phenyl substituted by 1 to 3 $C_1$-$C_4$-alkyl, $C_1$-$C_4$-alkoxy and halogen radicals or naphthyl by transesterification of aromatic hydroxyl compounds of the formula $$Ar^1OH \qquad (II),$$

in which $Ar^1$ has the meaning given with 0.1 to 10 mol, preferably with 0.5 to 2 mol and particularly preferably with 0.8 to 1.2 mol, of dialkyl carbonates of the formula $$R^1\text{—}O\text{—}CO\text{—}O\text{—}R^1 \qquad (III)$$

in which $R^1$ denotes straight-chain or branched $C_1$-$C_6$-alkyl or $C_5$-$C_6$-cycloalkyl, in the presence of transesterification catalysts known per se in column apparatuses as are known for transesterification reactions, which is characterised in that the reaction is carried out in a mass-coupled and energy-coupled combination of a counter-current column A and a reaction column B, reactions and separations running in parallel in the mentioned apparatuses, in such a way that, in the counter-current column A, the aromatic hydroxyl compounds which were withdrawn at least in part in the liquid state from the reaction column B is reacted in the liquid phase in the presence of a transesterification catalyst with a mixture, conducted in counter-current thereto in the gaseous state, of 100 to 95 parts by weight of dialkyl carbonate and 0 to 5 parts by weight of the underlying alcohol of the formula $$R^1OH \qquad (IV)$$

in which $R^1$ has the given meanings, where the mixture was withdrawn in the gaseous state from the reaction column B and can contain aromatic hydroxyl compounds $Ar^1OH$, at temperatures from 100° to 300° C. and pressures from 0.05 to 20 bar and the mixtures, produced in A as a bottom product, of alkyl aryl carbonates of the formula $$Ar^1\text{—}O\text{—}CO\text{—}O\text{—}R^1 \qquad (V),$$

in which $Ar^1$ and $R^1$ have the meaning given above, or unreacted aromatic hydroxyl compounds, with or without a small amount of the dialkyl carbonate and with or without homogeneously dissolved catalyst in the liquid form, are fed into the bottom part of the reaction column B and the gaseous mixtures, produced in A as head products, of the alcohols, as yet unreacted dialkyl carbonate and aromatic hydroxyl compounds are fed into the upper part of the reaction column B and are reacted at temperatures of 100° to 300° C. and pressures of 0.05 to 5 bar to the extent of 50 to >95%, where, furthermore, diaryl carbonate is withdrawn as a bottom product in the lower part of the column B, the liquid stream, which is to be returned to A, of the aromatic hydroxyl compounds is withdrawn in the central section of B and above the feed of the bottom product of A, the gaseous mixture, which is to be returned to A, of 95 to 100 parts by weight of dialkyl carbonate and 0 to 5 parts by weight of the alcohols derived therefrom and of the aromatic hydroxyl compound is withdrawn in the central section of B between the draw-off of the liquid aromatic hydroxyl compounds and the infeed of the head product from A, and a mixture of 80 to 20% by weight of the derived alcohols and 20 to 80% by weight of dialkyl carbonate is withdrawn as a head stream from B, reacted or withdrawn dialkyl carbonate and reacted aromatic hydroxyl compounds being supplemented by feed into A or B.

DETAILED DESCRIPTION OF THE INVENTION

Figure 1:
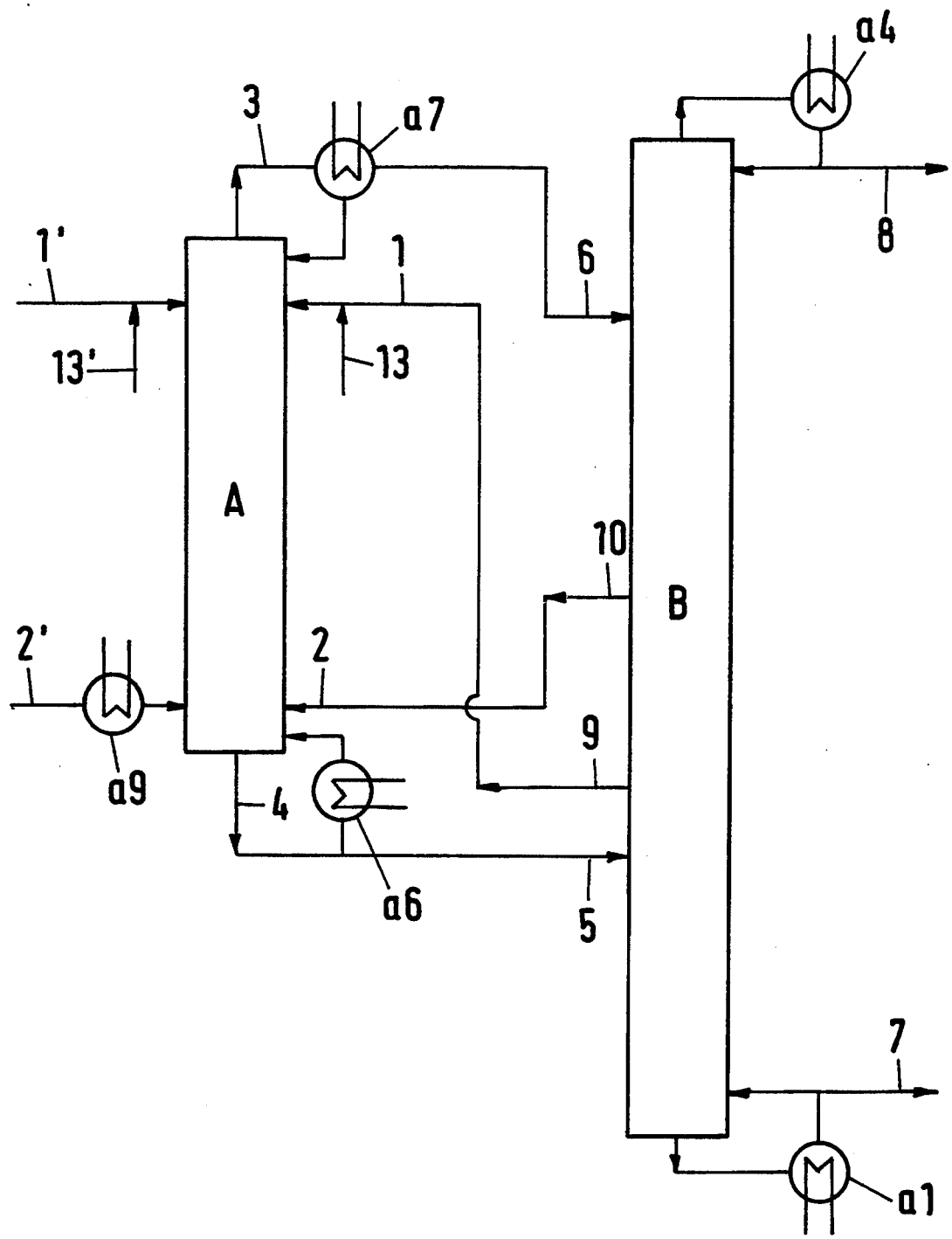
FIG. 1, 2 and 3 show different embodiments of combination of a first column A operated in the sense of a counter-current technique with a second column B operated in the sense of a reaction distillation.

Diaryl carbonates which can be prepared according to the invention are therefore compounds of the formula $$Ar^1\text{—}O\text{—}CO\text{—}O\text{—}Ar^1 \qquad (I),$$

in which $Ar^1$ has the above meaning, for example diphenyl carbonate, the isomeric bis-tolyl carbonates, the isomeric bis-(ethylphenyl) carbonates, the isomeric bis-(chlorophenyl) carbonates, the isomeric bis-(bromophenyl) carbonates, the isomeric bis-(methoxyphenyl) carbonates, bis-(1-naphthyl) carbonate, bis-(2-naphthyl) carbonate and bis-(1,6-dimethylphenyl) carbonate, preferably diphenyl carbonate and bis-(tolyl) carbonate and particularly preferably diphenyl carbonate.

Aromatic hydroxyl compounds which can be used are therefore those of the formula $$Ar^1OH \qquad (II),$$

in which $Ar^1$ has the above meaning.

Examples which can be mentioned are phenol, the isomeric cresols, the isomeric ethylphenols, the isomeric chlorophenols, the isomeric bromophenols, the isomeric methoxyphenols, the isomeric naphthols and xylenols. Phenol and the cresols can particularly preferably be used. Phenol itself can very particularly preferably be used.

According to the invention, dialkyl carbonates of the formula

$$R^1-O-CO-O-R^1 \quad \text{(III)}$$

are used, in which $R^1$ has the above meaning, for example dimethyl carbonate, diethyl carbonate, dipropyl carbonate, dibutyl carbonate, dihexyl carbonate, dicyclohexyl carbonate and dicyclopentyl carbonate. Dimethyl carbonate and diethyl carbonate can particularly preferably be used and dimethyl carbonate can very particularly preferably be used.

Straight-chain or branched $C_1$-$C_6$-alkyl is, for example, methyl, ethyl, propyl, isopropyl, butyl, isobutyl, pentyl or hexyl.

Straight-chain or branched $C_1$-$C_4$-alkoxy is, for example, methoxy, ethoxy, propoxy, isopropoxy, butoxy or isobutoxy.

Halogen is, for example, fluorine, chlorine or bromine, preferably fluorine or chlorine, particularly preferably chlorine.

The reactor designated Column A is mainly operated in this case in a counter-current technique, that is, a liquid aromatic hydroxyl compound which flows down from the head of the column is reacted on the main column section with dialkyl carbonate which is conducted in the opposite direction in the gaseous state, both starting materials being withdrawn from a second reactor B at a suitable position. The alkyl carbonate formed is withdrawn at the foot of the column A, if appropriate, together with not reacted aromatic hydroxy compound and dialkyl carbonate, the readily volatile reaction alcohol is withdrawing in a mixture with unreacted dialkyl carbonate and the aromatic hydroxyl compound at the head of the column A. A preferred technique dispenses with returning significant proportions of the as yet unreacted phenol to the reactor by evaporation at the foot of the column and returning significant proportions of the as yet unreacted dialkyl carbonate by reflux at the head of the column, so that the energy input and the energy withdrawal at this position of the process remain relatively low. The product/starting material streams produced at the head and at the foot of the column A are conducted at a suitable position into the column-like reactor B.

In this reactor B, the alkyl aryl carbonate produced in the reactor A is further reacted in the sense of a "reaction distillation". The essential characteristics for a "reaction distillation" in the sense of the invention are the following: the alkyl alkyl carbonate, by a specially chosen temperature gradient, is substantially prevented from leaving the reaction zone of the reactor at the top or at the bottom. The readily volatile reaction products, here reaction alcohol, dialkyl carbonate and excess phenol, are transported into the upper and central region of column B; the poorly volatile reaction product, here the diaryl carbonate, is withdrawn at the foot of the column via (6).

In reactor B, still further separation processes proceed simultaneously which permit the still unreacted aromatic hydroxyl compounds and low-alcohol and high-alcohol dialkyl carbonate/alcohol mixtures to be withdrawn from the reactor at positions separated from each other, the high-alcohol dialkyl carbonate fraction being withdrawn at the head of column B as a low-boiling product. The low-alcohol dialkyl carbonate fractions and the aromatic hydroxyl compounds are returned into reactor A.

The starting materials required for column A and for column B are thus alternately obtained from the respective coupled reactor. The starting materials which are lost to the overall process by reaction or by discharge together with the products can be fed in either directly into reactor A in the sense of the above-described counter-current technique or, preferably, into the central or upper part of the reactor B (see FIGS. 1 and 2).

The majority of the energy for the overall process is introduced in the lower part of reactor B, serves there for the reaction to form the diaryl carbonate, is brought by the excess, back-distilling aromatic hydroxyl compound into the central and upper region of the column and there drives the above-described separations. At the same time, the energy from column B can be used for the operation of column A via the starting material streams returned from reactor B to A.

By the above-described procedure, which is adapted to the specific transesterification problem, in two mass-coupled and energy-coupled column-type reactors, without isolation of the alkyl aryl carbonate intermediates, high conversion rates of the aromatic hydroxyl compounds and of the dialkyl carbonates are simultaneously achieved. The products withdrawn at the foot and at the head of the reactor B are already enriched to a great extent and are thus easy to purify or can be returned directly into connected coupled processes, for instance for renewed preparation of dimethyl carbonate. For example, at the head of reactor B, methanol/-dimethyl carbonate mixtures are obtained which virtually already have the composition of the methanol/-dimethyl carbonate azeotrope of 30:70% by weight and can be used without further concentration in a transesterification process for the preparation of dimethyl carbonate. Furthermore, it is possible to introduce alcohol-containing dialkyl carbonates into the process according to the invention. The energy is essentially introduced at one position of the process, that is at the bottom end of the reactor B, and is also essentially withdrawn again at one place, at the head of the column B, and repeatedly utilised internally for various process steps, i.e. optimal energy utilisation is possible with the process according to the invention.

The reactor A termed a "counter-current column" represents in the simplest case an isothermically heated or, preferably, adiabatically insulated tube furnished with conventional dumped packings, arranged packings or column internals to be used for distillations.

At the bottom end, the column can have a stripping valve operating at elevated temperatures in which a substantial to complete separation of the fed-in dialkyl carbonate from the liquid phase trickling down is carried out, the dialkyl carbonate being conducted again in the vapour phase into the transesterification region of the column. In addition, the column, at the upper part, can have an enrichment section which separates off co-evaporated phenol or alkyl phenyl carbonate from the low-boiling reaction alcohols or dialkyl carbonates and returns it in the liquid state into the transesterification section of the column.

However, in a preferred technique such enrichment sections or stripping sections can be dispensed with at these positions.

In the context of the process according to the invention it is expedient to introduce the energy necessary for the reaction not only via jacket heating or via other heat exchangers, but both with the phenol used and with the dialkyl carbonate fed in in gaseous form. The evaporation energy for the dialkyl carbonate can, if desired, be applied via a separate evaporator or an evaporator integrated into the column. In addition, internal or external heat exchangers can be built into the column to compensate for heats of reaction. The column may exhibit either the same temperature or a temperature gradient over its entire length. The design of the transesterification, stripping and enrichment section can be carried out by those skilled in the art.

The dumped packings or arranged packings to be used are those conventional for distillations, such as are described, for example, in Ullmann's Encyclopädie der Technischen Chemie [Ullmann's Encyclopedia of Industrial Chemistry], 4th edition, volume 2, pp. 528 ff. or in the company leaflets of the relevant apparatus engineering companies. Examples which can be mentioned are: Raschig or Pall rings, Berl, Intalox or toroidal saddles, Interpack packings made of various materials, such as glass, stoneware, porcelain, stainless steel, plastic, which, in particular when metal is used, can be processed into a fabric or mesh form. Dumped packings and arranged packings are preferred which have a large surface area and show good wetting and sufficient residence time of the liquid phase.

These are, for example, Pall and Novolax rings, Berl saddles, BX packings, Montz-Pak, Mellapak, Melladur, Kerapak and CY packings.

However, for the process according to the invention, in particular for the reactor A, not only are packed columns suitable but also those having fixed internals. Tray columns are generally suitable, for example those having sieve trays, bubble-cap trays, valve trays, tunnel trays and centrifugal trays, which in turn can, moreover, be present in various configurations. Among these, those having bubble-cap trays or valve trays with high residence times and with good mass transfer, for example bubble-cap tray columns having high overflow weirs, as described, for example, in DE-OS (German Published Specification) 2503195, are preferred.

The theoretical plate number of the column to be used as reactor A is 3 to 50, preferably 3 to 30 and particularly preferably 5 to 20 plates; the liquid holdup is 1 to 80%, preferably 5 to 75% and particularly preferably 10 to 50% of the column internal volume. More precise design of the transesterification section and the stripping section and enrichment section possibly to be used can be made by those skilled in the art.

The column A is operated within the overall process (FIGS. 1 to 3) in such a way that in the upper half, preferably in the upper third, and particularly preferably on the top tray or at the head of the packing, a phenol stream originating from the column B is fed in in the liquid state via (1), preferably at the temperature prevailing at this position of the column. This phenol stream can, possibly, contain low concentrations of dialkyl carbonate and alcohol which correspond to the solubility of these components in the corresponding phenol at the given temperature. The desired temperature can be established with the aid of a separate heat exchanger. However, the phenol is preferably withdrawn from column B at (9) and fed to column A at (1) without further heating or cooling.

Into the bottom half of column A, preferably above a stripping zone which may be present, a dialkyl carbonate stream which is withdrawn from column B at (10) is fed in via (2), generally in vapour form, at temperatures from 120° to 220° C. This dialkyl carbonate stream contains 0 to 5% by weight, preferably 0.1 to 3% by weight and particularly preferably 0.2 to 2% by weight, of the corresponding alcohol, and considerable amounts of a phenol.

After passing through the transesterification zone and possibly after passing through an enrichment zone, the reaction alcohol is withdrawn at the head of the column at (3). It generally still contains excess or unreacted dialkyl carbonate and, when an enrichment section is not present, also relatively large amounts of the aromatic hydroxyl compound. This head stream is preferably conducted, without previous condensation, in the gaseous state into column B at (6).

After passing the transesterification zone and a stripping section which may be present, a mixture of alkyl aryl carbonate with excess or unreacted phenol, with or without small amounts of diaryl carbonate already formed, with or without soluble catalysts and, in the case of a technique without a stripping section, also with dialkyl carbonate exits at the foot of the column A at (4). The bottom product is fed into the second transesterification column B directly via (5).

The catalyst is preferably introduced above or at the same height as the phenol feed (1) into column A at (13') in dissolved or suspended form, either with small amounts of phenol, with reaction alcohol or in a suitable inert solvent which is foreign to the system. The catalyst is particularly preferably fed in to the column A with the liquid phenol stream originating from the column B, where the catalyst can, for example, be introduced at (13) at the side into the phenol stream. When heterogeneous catalysts are used, these can be used in a mixture with the packings mentioned, in a suitable form instead of packings or as a bed on built-in column trays.

The molar ratio of the starting materials used in the column A varies from 0.1 to 10 mol, preferably from 0.2 to 5 mol and particularly preferably from 0.5 to 3 mol of dialkyl carbonate per mole of phenol used.

The transesterification in the reactor A can be carried out at temperatures from 100° to 300° C., preferably at temperatures from 120° to 250° C. and particularly preferably at temperatures from 140° to 230° C. in the column. The slight temperature gradient present lies in the given temperature range and increases from the column head in the direction of the column foot. In this case, it must be ensured that the reaction temperature in the transesterification region does not lie above the evaporation temperature of the phenol used. It is therefore advantageous to carry out the transesterification according to the invention not only at atmospheric pressure, but alternatively at elevated or reduced pressure from 50 mbar up to 20 bar. A preferred pressure range lies between 0.2 and 12 bar, a particularly preferred pressure range lies between 0.5 and 10 bar.

The space-time loading of the column A lies at 0.25 to 3 g of total amount of reactants per ml of effective column volume per hour, preferably at 0.05 to 3 g/ml/h, particularly preferably at 0.1–2 g/ml/h; the effective column volume in this case is that of the packing or the volume in which fixed internals are located.

The reactor B (FIGS. 1 to 3) designated as "reaction column" is composed of a column-like tube to which a temperature profile is applied which, increasing as viewed from top to bottom, includes a temperature range from 50° to 320° C. preferably 60° to 300° C. To adjust the temperature gradients in the individual sections of the column-like reactor, these sections can be furnished with insulation or thermostating. The thermostating in this case, according to requirement, can represent heating or cooling (a2 and a3). The reactor B can be expanded or constricted in various sections of its overall length, corresponding to the gas loads and liquid loads and the residence times required.

The column tube of reactor B can be packed with conventional dumped or arranged packings to be used for distillations and may also possess fixed internals, with—preferably—different types of dumped packings, arranged packings or fixed internals able to be employed in the individual column regions. The dumped packings or arranged packings to be used are those conventional for distillations, such as are described, for example, in Ullmanns Encyclopädie der Techn. Chemie [Ullmanns Encyclopedia of Industrial Chemistry], 4th edition, volume 2, pp. 528 ff. or in the company leaflets of the relevant apparatus engineering companies. Examples which can be mentioned are: Raschig or Pall rings, Berl, Intalex or toroidal saddles, Interpack packings made of various materials, such as glass, stoneware, porcelain, stainless steel, plastic, which, in particular when metal is used, can be processed into a fabric or mesh form. Dumped packings and arranged packings which are preferred are, for example, Pall and Novolax rings, Berl saddles, BX packings, Montz-Pak, Metallpak, Melladur, Kerapak and CY packings.

However, for the reactor B, not only are packed columns suitable but also those having fixed internals. Those conventional in tray columns are generally suitable, for example sieve trays, bubble-cap trays, valve trays, tunnel trays and centrifugal trays, which can, moreover, be present in various configurations. Among these, bubble-cap trays or valve trays having high residence times with good mass transfer, for example bubble-cap tray columns having high overflow weirs, are preferred.

For the reaction region of column B, fixed internals are preferred; for the parts in which separations take place, on the other hand, dumped packings and fixed packings are preferred.

At the bottom end of the column B, one or more evaporators, possibly separated by adiabatically insulated column parts, are arranged. These evaporators can be arranged inside or, preferably, outside the column. In an industrial embodiment of the invention, apparatuses conventional in the technology such as circulation evaporators, falling-film evaporators and spiral tube evaporators are used.

Above the evaporator zone, in the central region termed the "reaction zone", fixed internals are preferably used, and particularly preferably those having large liquid holdup, for example bubble-cap trays having high overflow weirs. The theoretical plate number in this region is 2 to 50, preferably 2 to 25 and particularly preferably 2 to 15. The liquid holdup in this region is 5 to 80%, preferably 10 to 75% and particularly preferably 15 to 50% of the internal volume of the internals.

Again, above this region, the column is equipped with other packings or internals which are specially suitable for material separations by distillation. At the upper end of the column B, an enrichment section is arranged by which a specific reflux to the column can be established. In a preferred embodiment of the invention, the majority of the energy required for the overall process is introduced into the process by the evaporator arranged at the bottom end of column B and the majority of the excess energy is withdrawn again by the enrichment section arranged at the upper end of the reactor B. This energy is utilised internally for separations and the reactions proceeding in columns A and B.

The column B, within the overall process (FIGS. 1 to 3), is operated in such a way that into the central part of the column above the region termed a "reaction zone" via the feed (5), a stream withdrawn from column A at (4) and composed of alkyl aryl carbonate and aromatic hydroxyl compound, which can possibly contain small amounts of diaryl carbonate, dialkyl carbonate and a transesterification catalyst, is fed in in the liquid state. This stream passes through the "reaction zone" and is there partly converted into diaryl carbonate, and the still unreacted reactants are transported with the aid of the described evaporators in the gaseous state back into the central and upper parts of the column B. These condense there and react again to form the diaryl carbonate end product. The diaryl carbonate end product is enriched as the highest boiling reaction component in the bottom region of the column and is there discharged via (7) together with, possibly, homogeneously dissolved catalyst and small amounts of alkyl aryl carbonate and aromatic hydroxyl compound. The associated bottom circulation heater is (a1).

A product stream described above, which is withdrawn as a head product from column A at (3), is fed, preferably in the gaseous state, into the upper half, preferably the upper third, of the column B via (6). This product stream is split in the upper part of column B into (i) mixtures of 80 to 20% by weight of an alcohol of the formula (IV) and 20 to 80% by weight of a dialkyl carbonate of the formula (III) and, preferably, into mixtures of 30 to 70% by weight of an alcohol of the formula (IV) and 70 to 30% by weight of a dialkyl carbonate of the formula (III) and (ii) mixtures of 95 to 100% by weight of dialkyl carbonate (III) and 0 to 5% by weight of an alcohol of the formula (IV) and, preferably, into mixtures of 97 to 99.8% by weight of (III) and 3 to 0.2% by weight of (IV). The mixture (ii), additionally to the composition given and above the 100% mark, also always contains the aromatic hydroxyl compound. For this separation, a column region having 10 to 50 theoretical plates and, preferably, having 10 to 30 theoretical plates is required, where the separation can be influenced by a specifically adjustable reflux. The higher-alcohol part-stream (i) is withdrawn (condenser a4) via the head at (8) and can be fed either to further work-up or, possibly, when the alcohol concentration is suitable, directly to an upstream transesterification process for the preparation of dialkyl carbonate. The low-alcohol part-stream (ii) is withdrawn via (10) beneath the indicated separation region and is returned into the column A, as described above, in the gaseous state at (2). The energy for the above-described separation by distillation and for the superheating of the gas stream (10) to (2) is essentially supplied by the phenol and alkyl aryl carbonate which distil at high temperature from the foot of column B and condense again in the central region of the column B. If required, a further heat exchanger in the central region of the column can serve to support these processes (a2 or a2 and a3 in FIGS. 2 and 3).

The condensing phenol of the formula (II) is withdrawn in the liquid state at temperatures just beneath its boiling point at a suitable point (9) of the column B beneath the draw-off position of the dialkyl carbonate stream (10) and, as described above, returned at (1) in the liquid state into column A. A column section having 2 to 20, preferably 3 to 10, plates is required for the resolution of this phenol stream. It can, moreover, be expedient to divide the reactor on the gas side between the feed position (6) and the gas draw-off position (10) and to make possible at this position of the column B only a liquid stream from top to bottom, the gas stream and energy stream then being conducted with the aid of a controllable steam division partly via (10) to (2), into the column A and via (3) to (6) into the upper part of the column B. This can be made possible, for example, by a special intermediate plate between (9) and (10).

In a particular technique (FIG. 3), the crude product mixture (7), which is essentially composed of diaryl carbonate, can be still further reacted and separated in a downstream separate reactor C at pressures from 0.05 to 1.0 bar, pure diaryl carbonate being withdrawn in the side stream of this column via (15), a diaryl carbonate-containing catalyst bottom product (16) being withdrawn at the foot of the column and the unreacted starting materials and low-boiling product formed being withdrawn via the head at (14). The catalyst bottom product (16) can be returned at a suitable position into the process, for example into the reactor A at the above-mentioned position (13, 13') or into the reactor B (13''). If partial deactivation takes place, it is, of course, also possible to withdraw (16') a part of the catalyst bottom product and to replace the removed part of the catalyst by fresh catalyst at a suitable position. The mixture produced as the head product of the column C can be returned via the product stream (4) to (5), possibly after equalisation of the pressure, into the transesterification process.

When homogeneously dissolved or suspended catalysts are used, the catalysts which are already active in column A and which are contained in the bottom product (4) are essentially fed into column B at (5) and as a result are active in the reactor zone of B. However, there is additionally the possibility, at a position below the dialkyl carbonate removal site (10), to feed in additional catalyst of the same type or a second catalyst (13''). When heterogeneous catalysts are used, these can be used in a mixture with the mentioned packings, in a suitable form instead of packings or preferably as a bed on built-in column trays.

The reaction in column B is carried out at a pressure between 50 mbar and 5 bar preferably between 0.1 and 3 bar, particularly preferably between 0.2 and 2 bar, and very particularly preferably at ambient pressure. The temperatures in the region of column B which is designated the reaction zone lie between 100° and 300° C., preferably between 120° and 280° C. and particularly preferably between 140° and 260° C.

Figure 3:
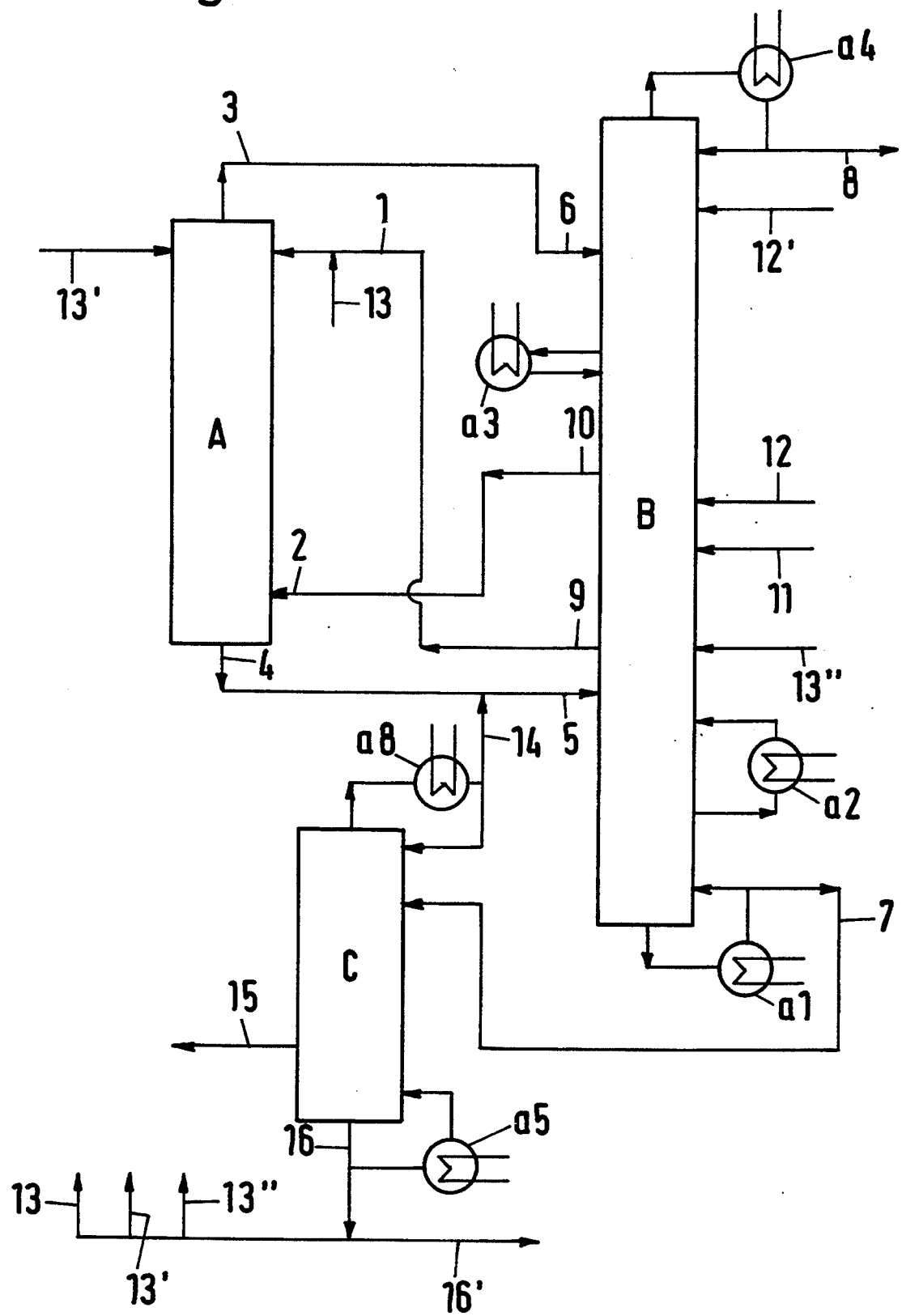

The educts which have reacted to form products and thus are consumed or have been ejected from the process together with the products via (7) or (8) can be fed either into the column A in the sense of a counter-current transesterification, the phenols being introduced in the liquid state at the upper end of the column as (1') and the diaryl carbonates being introduced in the gaseous state at the foot of the column A as (2'). However, preferred feed positions for the phenols (11) and dialkyl carbonates (12) are in the central and upper region of the column B, where at this position, apart from pure dialkyl carbonate and mixtures having the abovementioned amount of from 0 to 5% by weight of the underlying alcohol, it is also possible to use mixtures of dialkyl carbonates and alcohols having up to 20% by weight, preferably up to 10% by weight, of alcohol. It is even possible to use mixtures of dialkyl carbonates and up to 60% by weight of the corresponding alcohol, if these are added to column B at a position (12') above the vapour feed (6) from the column A, as indicated in FIG. 3. Preferred amounts of alcohol are 0.5 to 20% by weight, particularly preferably 1 to 10% by weight, based on the total weight of the mixture.

In FIG. 1 and FIG. 3, (a6) and (a5) are conventional bottom circulation heaters for columns A and C, respectively; (a7) and (a8) are condensers having reflux dividers on the columns A and C, respectively; (a9) is an evaporator for dialkyl carbonate which is fed into column A at (2') (FIG. 1).

Figure 2:
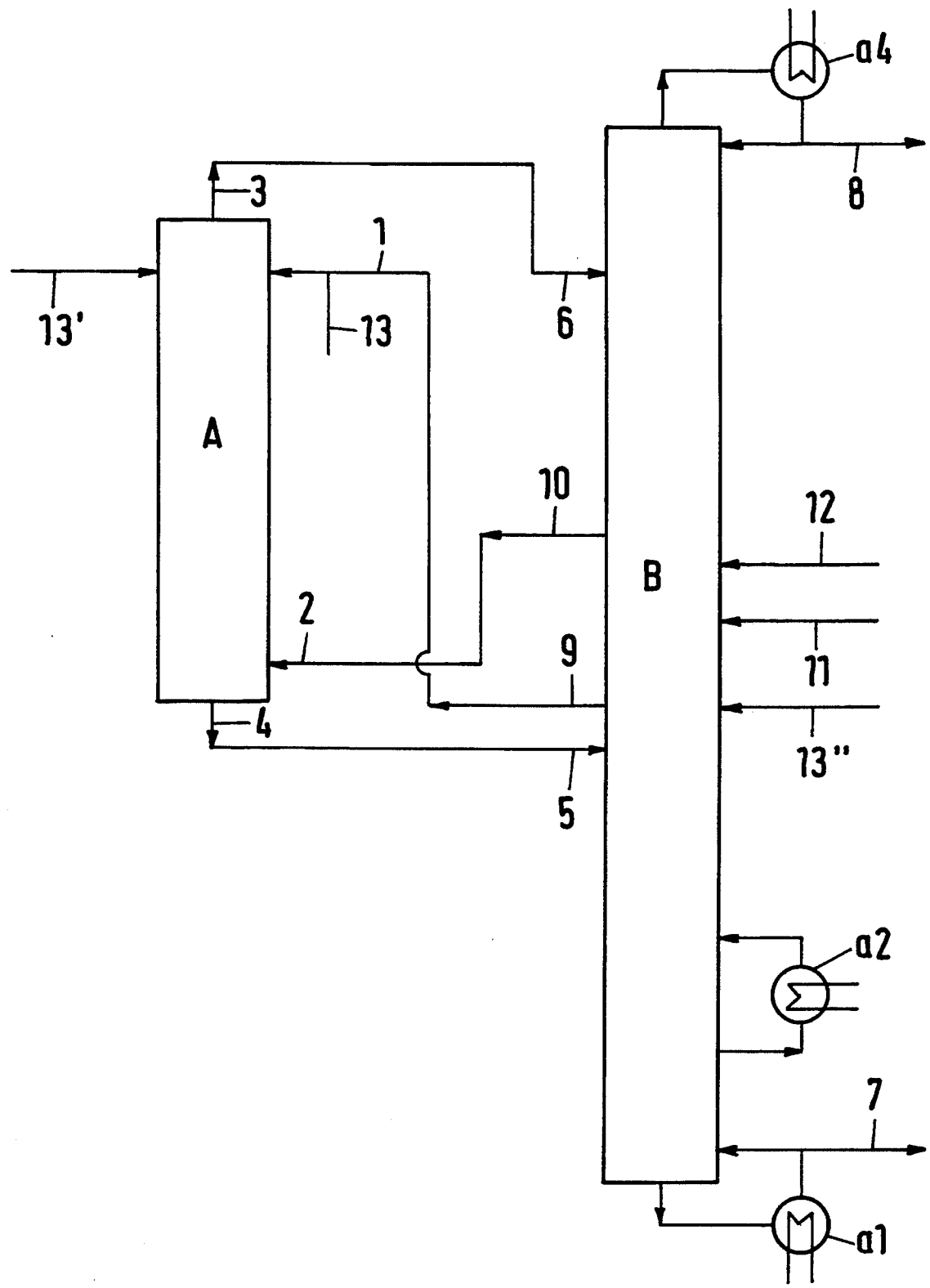
Figure 4:
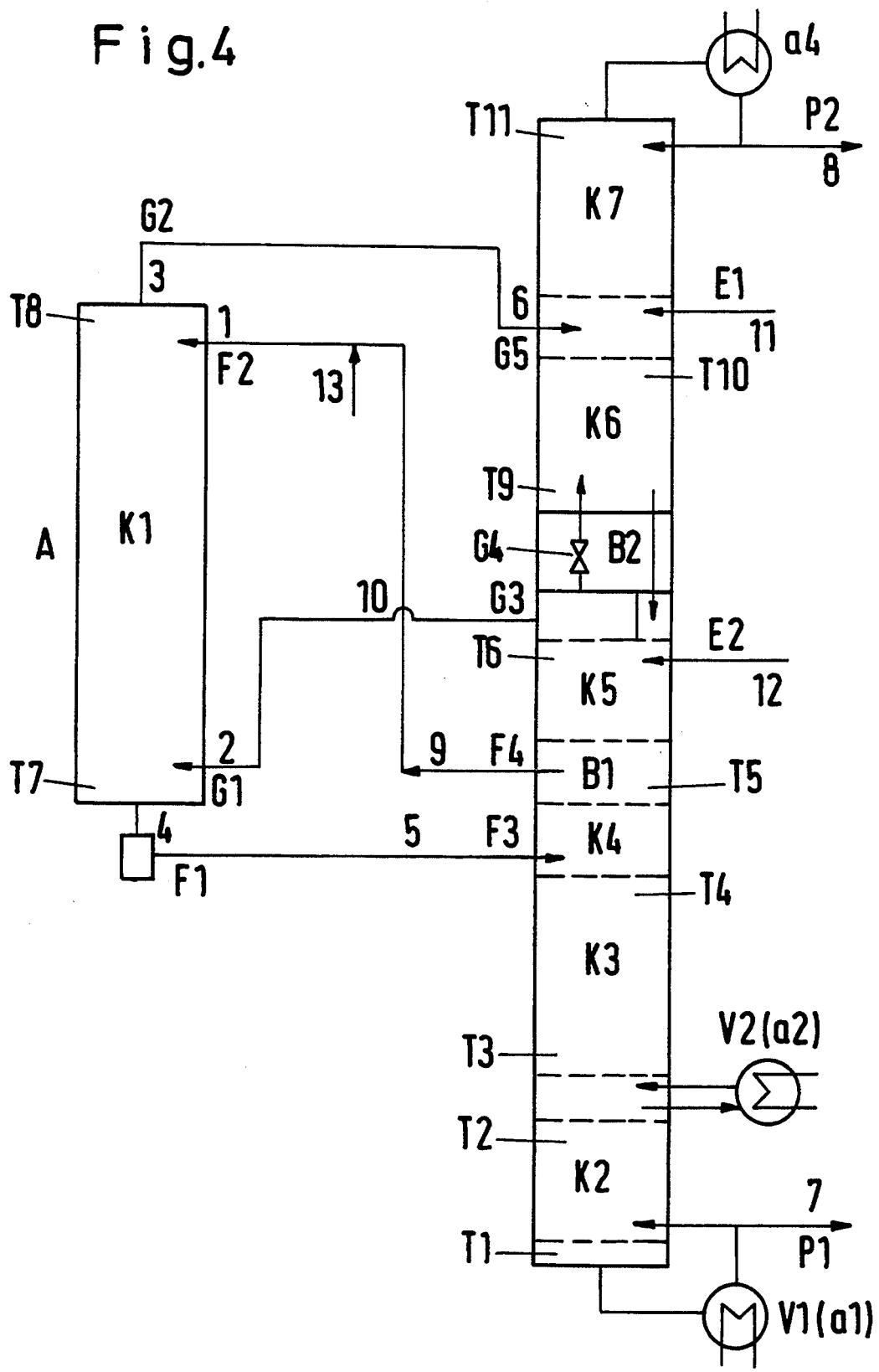
FIG. 4 shows in addition to FIG. 2 further details, mainly of column B, to which reference is made in the working examples.

FIG. 4 shows further details supplementing FIG. 2 which are described in the context of the exemplary embodiments.

For all reaction steps according to the invention, the same catalysts can be used. These are transesterification catalysts known from the literature for the dialkyl carbonate/phenol transesterification, such as for example hydrides, oxides, hydroxides, alcoholates, amides and other salts of alkali metals and of alkaline earth metals (U.S. Pat. No. 3,642,858; U.S. Pat. No. 3,803,201; EP 1082), such as of lithiums, sodium, potassium, rubidium, caesium, magnesium and calcium, preferably lithium, sodium, potassium, magnesium and calcium and particularly preferably lithium, sodium and potassium. Salts of the alkali metals and of the alkaline earth metals can also be those of organic or inorganic acids, such as of acetic acid, propionic acid, butyric acid, benzoic acid, stearic acid, carbonic acid (carbonates or hydrogencarbonates), phosphoric acid, prussic acid, thiocyanic acid, boric acid, stannic acid, $C_1$-$C_4$-stannonic acids or antimonic acid. Compounds of the alkali metals and of the alkaline earth metals which are useful are preferably the oxides, hydroxides, alcoholates, acetates, propionates, benzoates, carbonates and hydrogencarbonates; particularly preferably hydroxides, alcoholates, acetates, benzoates or carbonates are used.

The alkali metal compounds or alkaline earth metal compounds mentioned are used in amounts of 0,001 to 2% by weight, preferably 0.005 to 0.9% by weight and particularly preferably 0.01 to 0.5% by weight, based on the reaction mixture to be reacted.

Further catalysts which can be used according to the invention are Lewis acid metal compounds such as $AlX_3$, $TiX_3$, $UX_4$, $TiX_4$, $VOX_3$, $VX_5$, $ZnX_2$, $FeX_3$ and $SnX_4$, in which X represents halogen, acetoxy, alkoxy or aryloxy (DE-OS (German Published Specification) 2 528 412, 2 552 907), for example titanium tetrachloride, titanium tetraphenoxide, titanium tetraethoxide, titanium tetraisopropylate, titanium tetradodecylate, tin tetraisooctylate and aluminium triisopropylate, in addition organotin compounds of the general formula $(R^{11})_{4-x}$—$Sn(Y)_x$, in which Y represents a radical $OCOR^{12}$, OH or OR, where $R^{12}$ denotes $C_1$-$C_{12}$-alkyl, $C_6$-$C_{12}$-aryl or $C_7$-$C_{13}$-alkylaryl and $R^{11}$, independently of $R^{12}$, has the meaning of $R^{12}$ and x denotes an integer from 1 to 3, dialkyltin compounds having 1 to 12 C atoms in the alkyl radical or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid and octylstannonic acid in amounts of 0.001 to 20% by weight (EP 879, EP 880, EP 39 452, DE-OS (German Published Specification) 3 445 555, JP 79/63023), polymeric tin compounds of the formula —[—R,R$^{11}$Sn—O—]—, for example poly[oxy(dibutylstannylene)], poly[oxy(dioctylstannylene)], poly[oxy(butylphenylstannylene)] and poly[oxy(diphenylstannylene)] (DE-OS (German Published Specification) 3 445 552), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxanes) in amounts of 0,001 to 20% by weight, preferably of 0,005 to 5% by weight, based on diesters of carbonic acid (DE-OS (German Published Specification) 4 006 520).

Further tin compounds which can be used according to the invention are Sn(II) oxides and have the formula

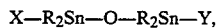

$$X—R_2Sn—O—R_2Sn—Y,$$

in which X and Y, independently of each other, are to denote OH, SCn, OR$^{11}$OCOR$^{11}$ or halogen and R is to denote alkyl, aryl (EP 0 338 760).

Further catalysts which can be used according to the invention are lead compounds, with or without triorganophosphines, a chelate compound or an alkali metal halide, for example Pb(OH)$_2$.2PbCO$_3$, Pb(O-CO—CH$_3$)$_2$, Pb(OCO—CH$_3$)$_2$2LiCl, Pb(O-CO—CH$_3$)$_2$.2PPh$_3$ in amounts from 0.001 to 1, preferably from 0,005 to 0.25, mol per mole of carbonate (JP 57/176932, JP 01/093580), other lead(II) compounds and lead(IV) compounds, such as PbO, PbO$_2$, red lead, plumbites and plumbates (JP 01/093560), iron(III) acetate (JP 61/172852), furthermore copper salts and/or metal complexes, for example of alkali metal, zinc, titanium and iron (JP 89/005588), combinations of Lewis acids and protonic acids (DE-OS (German Published Specification) 3 445 553) or element compounds of Sc, Cr, Mo, W, Ha, Au, Ga, In, Bi, Te and lanthanides (EP 338 760).

Furthermore, heterogeneous catalyst systems can be used in the processes according to the invention. Such heterogeneous catalyst systems are, for example, mixed oxides of silicon and titanium, which can be prepared by collective hydrolysis of silicon and titanium halides (JP 54/125617), and titanium dioxides having a high BET surface area >20 m$^2$/g (DE-OS (German Published Specification) 4 036 594)).

Catalysts which can preferably be used in the process according to the invention are tin compounds, titanium compounds and zirconium compounds and the above-mentioned alkali metal compounds and alkaline earth metal compounds; particularly preferably usable catalysts are organotin compounds and titanium tetraalkyl esters and titanium tetraaryl esters.

In some cases the amounts of catalysts which are to be used can differ from the amounts mentioned in the literature.

EXAMPLES 1-4

Transesterification in a combination of a counter-current transesterification column A and a reaction column apparatus B (see FIG. 4 as a specific embodiment of FIG. 2) having the following construction, where, in addition to the designations given above, further symbols are given:

Counter-current column A

Construction described from bottom to top:
F1: liquid bottoms draw-off via a 20 cm-long siphon at the base of the column;
G1: feed position for gaseous dialkyl carbonate stream from apparatus B at the bottom end of column A
K1: insulated glass tray column of internal diameter 12 cm and having 10 bubble-cap trays 12×10 cm (tray measurement).
F2: introduction point for liquid phenol stream from column B at the top end of column A
G2: gaseous head product draw-off via insulated glass tube to the column apparatus B.

Reaction column apparatus B:

Construction described from bottom to top:
Falling-film evaporator (approximately 0.1 m$^2$ evaporation surface) having a level-controlled high-boiling product draw-off (P1) at the bottom end and an insulated glass elbow as a connection piece to column K2;
K2: Insulated tray column having internal diameter 10 cm and 5 bubble-cap trays 10×10 cm and a temperature measuring point T1;
V2: Oil-thermostated intensive cooler having a length of 30 cm and an internal diameter of 7.5 cm, having 2 internal evaporator coils each of 1 cm in diameter (evaporator surface approximately 0.15 m$^2$) and internal temperature measuring points at the bottom and top ends (T2, T3).
k3: Insulated tray column of internal diameter 10 cm with 10 bubble-cap trays 10×10 cm;
F3: Feed point for the liquid bottom product (F1) from column A;
k4: Insulated column section of length 55 cm and internal diameter 5 cm having a SULZER arranged packing DX.
B1: Special section for the ejection of the liquid phenol stream for the column A (length 30 cm, internal diameter 5 cm) having a 100 ml tray for phenol ejection (F4) between two 50 ml flow measurement trays for the measurement of the liquid stream;
K5: Insulated column of length 55 cm and internal diameter 5 cm having SULZER arranged packing DX;
E2: Dialkyl carbonate or dialkyl carbonate/alcohol feed position; (further up, for example near E1, when mixtures of starting materials having a relatively high alcohol content are used);
B2: Special tray having (i) gas take-off (G3) for column A, (ii) a line (G4) which is controllable by a valve, for the controllable conduction of a gas stream into the column K6 and (iii) a 50 cm-long variably adjustable siphon for returning the liquid stream from column K6;
K6: Insulated column of length 55 cm and internal diameter 5 cm having SULZER arranged packing DX;
G5: Gas inlet tube for gas stream from column A
E1: Phenol feed position;
Insulated section 120×5 cm, packed with a SULZER company EX arranged packing;
P2: Head product draw-off point with reflux condenser, reflux divider and reflux measurement.
K=column sections, V=evaporators/heat exchangers, B=special trays, F=liquid feed and draw-off points, G=gas feed and take-off points, E=starting material feeds, P=end product draw-off points, T=temperature measurement points (the measurement points not given in the text can be inferred from the drawing).

The head product draw-off point (G2) of the column A is connected via an insulated line to the gas inlet tube (G5) of the column apparatus B. The bottom product draw-off point (F1) of the column A is connected via an insulated line to the dosing feed point (F3) of the column B. The liquid take-off (F4) at the special tray (B1) of the apparatus B is connected via a heatable line having an intermediately connected metering pump to the dosing feed point (F2) of the column A.

The gas take-off (G3) at the special tray (B2) of the apparatus B is connected via an insulated line to the gas dosing feeder (G1) of the column A. The high-boiling product mixture is withdrawn at the foot of the apparatus B via (P1), the low-boiling product mixture is withdrawn via (P2) at the head of the apparatus B.

The experiments were carried out in the described plant according to the following technique:
Start-up procedure and operating conditions:

tion reducing with increasing $T_5$, and increasing with falling $T_5$.

The experimental conditions and experimental results are compiled in the table.

From the examples it is clear that with the aid of the process according to the invention, in a specific, mass-coupled and energy-coupled column combination, highly enriched diphenyl carbonate fractions and methanol fractions can be simultaneously obtained, whereas this is not possible by the prior art. As follows from Example 4, mixtures of dimethyl carbonate and methanol (here 8% by weight of methanol) can also be introduced at a suitable position into the process according to the invention without loss of yield. The energy introduced via the bottom evaporators of column B can be used freely to drive all reactions and transport processes and separation processes. Since all evaporation processes and condensation processes are directly coupled and at no point must condensation and reevaporation be carried out externally, an optional utilisation of the energy introduced is possible.

TABLE
(Examples 1–4)

| | Starting material dosing | | | Product take-off | | | | | | | | | |
|---|---|---|---|---|---|---|---|---|---|---|---|---|---|
| | | | | Head | | Bottom | | | | | | | |
| No. | E1 Phenol [g/h] | E2 DMC [g/h] | E3 Catalyst [Type (g/h)] | [g/h] | product P2 Composition [% by weight] | [g/h] | product P1 Composition [% by weight] | Selectivity [%] | \multicolumn{6}{c}{Controlled temperatures [°C.]} |
| | | | | | | | | | T1 | T2 | T5 | T7 | T9 | T11 |
| 1 | 307 | 235 | **SNcat (4.3) | 193 | Methanol/53 DMC/47 | 355 | DPC/96.1 Phenol/1.8 MPC/2.3 | 99.5 | 250 | 220 | 170 | 165 | 130 | 65.5–64.0 |
| 2 | 280 | 225 | Ti(OPh)4 (6.2) | 185 | Methanol/50 DMC/50 | 323 | DPC/95.7 Phenol/1.3 MPC/2.9 | 99 | 250 | 220 | 170 | 165 | 130 | 65.5–64.0 |
| 3 | 335 | 265 | Ti(OPh)4 (14.9) | 215 | Methanol/52 DMC/48 | 384 | DPC/95.7 Phenol/1.3 MPC/2.9 | 99 | 250 | 220 | 170 | 165 | 130 | 65.5–64.0 |
| 4 | *Phenol DMC 282 Methanol 24 | 307 | **Sncat. (4.3) | 260 | Methanol/48 DMC/52 | 352 | DPC/96.2 Phenol/1.8 MPC/2.0 | 99.5 | 250 | 220 | 175 | 167 | 120 | 65.5–64.0 |

*Mixture of phenol, DMC and methanol dosed in E1.
**Sncat. = poly(octylhydroxystannoxane)
DMC = Dimethyl carbonate, MPC = Methyl phenyl carbonate, DPC = Diphenyl carbonate 1. The plant is filled under nominal load with phenol via E1 at the preset pressure (in all examples atmospheric pressure) and with evaporators V1 and V2 set to 200° C., until a phenol reflux in the order of magnitude of the phenol dosing is present in the entire plant.

2. The phenol run via (F4) is set to the same value.

3. The catalyst dosing (via 13) and DMC dosing (E2) are fixed at a preset value.

4. At head temperatures $T_{11}$ between the values mentioned in the table, mixtures of methanol and dimethyl carbonate are withdrawn via P2 under temperature control and reflux control.

5. The temperature $T_9$ is adjusted to a preset value with the aid of a gas stream exiting from K5 which is controlled by the valve G4.

6. The phenol dosing (E1) is controlled via a preset value of the temperature $T_7$, the phenol dosing reducing with increasing $T_7$ and increasing with falling $T_7$.

7. By increasing the bottom evaporator temperatures V1 and V2, preset values of the temperatures $T_1$, $T_2$ and $T_3$ are set and diphenyl carbonate product mixtures are withdrawn at the foot of column B via P1.

8. The phenol circulation via (F4) is controlled via a preset value of the temperature $T_5$, the phenol circula-

We claim:
1. A process for the preparation of a diaryl carbonate of the formula

$$Ar^1-O-CO-O-Ar^1,$$

in which
Ar$^1$ denotes unsubstituted phenyl, phenyl substituted by 1 to 3 $C_1$–$C_4$-alkyl, $C_1$–$C_4$-alkoxy or halogen radicals, or naphthyl by transesterification of an aromatic hydroxyl compound of the formula $$Ar^1-OH,$$

Ar$^1$ has the meanings given,
with 0.1 to 10 mol of a dialkyl carbonate of the formula $$R^1-O-CO-O-R^1,$$

in which
R$^1$ denotes straight-chain or branched $C_1$–$C_6$-alkyl or $C_5$–$C_6$-cycloalkyl, in the presence of a transesterification catalyst in a column apparatus, wherein the reaction is carried out in a mass-coupled and energy-coupled combination of a counter-current column A and a reaction column B, reactions and separations running in parallel in the aforementioned columns, in such a way that, in the counter-current column A, the aromatic hydroxyl compound which was withdrawn at least in part in the liquid state from the reaction column B is reacted in the liquid phase in the presence of a transesterification catalyst with a mixture, conducted in counter-current thereto in the gaseous state, of 100 to 95 parts by weight of dialkyl carbonate and 0 to 5 parts by weight of the underlying alcohol of the formula $R^1OH$, in which $R^1$ has the given meaning, where the mixture was withdrawn in the gaseous state from the reaction column B and can contain aromatic hydroxyl compounds $Ar^1OH$, at temperatures from 100° C. to 300° C. and pressures from 0.05 to 20 bar and the mixture, produced in A as a bottom product, of an alkyl aryl carbonate of the formula $Ar^1-O-CO-O-R^1$, in which $Ar^1$ and $R^1$ have the meaning given above,
of unreacted aromatic hydroxyl compound, with or without a small amount of the dialkyl carbonate and with or without homogeneously dissolved catalyst in the liquid form, is fed into the bottom part of the reaction column B and the gaseous mixture, produced in A as head product, of the alcohol, as yet unreacted dialkyl carbonate and aromatic hydroxyl compound is fed into the upper part of the reaction column B and is reacted at temperatures of 100° to 300° C. and pressures of 0.05 to 5 bar in the reaction part of B to the extent of 60 to >95%, where, furthermore, diaryl carbonate is withdrawn as a bottom product in the lower part of the column B, the liquid stream, which is to be returned to A, of the aromatic hydroxyl compounds is withdrawn in the central section of B and above the feed of the bottom product of A; the gaseous mixture, which is to be returned to A, of 95 to 100 parts by weight of dialkyl carbonate and 0 to 5 parts by weight of the alcohols derived therefrom and aromatic hydroxyl compounds is withdrawn int he central section of B between the draw-off of the liquid aromatic hydroxyl compound and the infeed of the head product from A; and a mixture of 80 to 20% by weight of the derived alcohol and 20 to 80% by weight of dialkyl carbonate is withdrawn as a head stream from B, reacted or withdrawn dialkyl carbonate and reacted aromatic hydroxyl compound being supplemented by feed into A or B.

2. The process of claim 1, wherein the aromatic hydroxyl compound is transesterified with 0.2 to 2 mol of the dialkyl carbonate.

3. The process of claim 2, wherein the aromatic hydroxyl compound is transesterified with 0.8 to 1.2 mol of the dialkyl carbonate.

4. The process of claim 1, wherein the aromatic hydroxyl compound used is phenol or one of the isometric cresols.

5. The process of claim 4, wherein the aromatic hydroxyl compound used is phenol.

6. The process of claim 1, wherein dimethyl carbonate or diethyl carbonate is used.

7. The process of claim 6, wherein dimethyl carbonate is used.

8. The process of claim 1, wherein the reaction in column A is carried out at temperatures from 120° to 250° C.

9. The process of claim 8, wherein the reaction in column A is carried out at temperatures from 140° to 230° C.

10. The process of claim 1, wherein the reaction in column A is carried out at pressures from 0.2 to 12 bar.

11. The process of claim 10, wherein the reaction in column A is carried out at pressures from 0.5 to 10 bar.

12. The process of claim 10, wherein the reaction in column B is carried out at temperatures from 120°–280° C.

13. The process of claim 12, wherein the reaction in column B is carried out at temperatures of 140° to 260° C.

14. The process of clam 1, wherein the reaction in column B is carried out at pressures from 0.1 to 3 bar.

15. The process of claim 14, wherein, the reaction in column B is carried out at pressures from 0.2 to 2 bar.

16. The process of claim 1 wherein the column A is a tray column.

17. The process of claim 1, wherein the column B is configured in its reaction section as a tray column and in its distillation separation sections as a dumped-packed or arranged-packed column.

18. The process of claim 1, wherein, when the dialkyl carbonate is fed into column B, the permissible content of underlying alcohol in the mixture of dialkyl carbonate/alcohol can pass beyond the range from 0 to 5% by weight, based on the total weight of the mixture, and is 0 to 60% by weight.

19. The process of claim 18, wherein the underlying alcohol in the mixture of dialkyl carbonate/alcohol is 0.5 to 20% by weight.

20. The process of claim 19, wherein the underlying alcohol in the mixture of dialkyl carbonate/alcohol is 1 to 10% by weight.

* * * * *

UNITED STATES PATENT AND TRADEMARK OFFICE
CERTIFICATE OF CORRECTION

PATENT NO. : 5,334,742
DATED : August 2, 1994
INVENTOR(S) : Norbert Schon, et al.

It is certified that error appears in the above-identified patent and that said Letters Patent is hereby corrected as shown below:

Column 19, line 51, cancel "int he" and substitute --in the--.

Column 20, line 10, cancel "isometric" and substitute --isomeric--.

Signed and Sealed this

Fourteenth Day of December, 1999

Attest:

Q. TODD DICKINSON

Attesting Officer

Acting Commissioner of Patents and Trademarks